United States Patent
Santini, Jr. et al.

(10) Patent No.: US 8,095,197 B2
(45) Date of Patent: Jan. 10, 2012

(54) MEDICAL DEVICE FOR SENSING GLUCOSE

(75) Inventors: John T. Santini, Jr., North Chelmsford, MA (US); Stephen J. Herman, Andover, MA (US)

(73) Assignee: MicroCHIPS, Inc., Waltham, MA (US)

(*) Notice: Subject to any disclaimer, the term of this patent is extended or adjusted under 35 U.S.C. 154(b) by 2043 days.

(21) Appl. No.: 10/980,551

(22) Filed: Nov. 3, 2004

(65) Prior Publication Data
US 2005/0096587 A1  May 5, 2005

Related U.S. Application Data

(60) Provisional application No. 60/516,865, filed on Nov. 3, 2003, provisional application No. 60/577,720, filed on Jun. 7, 2004.

(51) Int. Cl.
*A61B 5/05* (2006.01)
*A61B 5/00* (2006.01)

(52) U.S. Cl. .......... 600/347; 600/309; 600/365

(58) Field of Classification Search .......... 600/347, 600/365
See application file for complete search history.

(56) References Cited

U.S. PATENT DOCUMENTS

| | | |
|---|---|---|
| 3,692,027 A | 9/1972 | Ellinwood, Jr. |
| 3,952,741 A | 4/1976 | Baker |
| 4,003,379 A | 1/1977 | Ellinwood, Jr. |
| 4,089,734 A | 5/1978 | Bierig |
| 4,209,894 A | 7/1980 | Keen |
| 4,345,981 A | 8/1982 | Bennett et al. |
| 4,360,019 A | 11/1982 | Portner et al. |
| 4,360,031 A | 11/1982 | White |
| 4,507,115 A | 3/1985 | Kambara et al. |
| 4,585,652 A | 4/1986 | Miller et al. |
| 4,731,049 A | 3/1988 | Parsi |
| 4,731,051 A | 3/1988 | Fischell |
| 4,793,825 A | 12/1988 | Benjamin et al. |
| 4,969,468 A | 11/1990 | Byers et al. |
| 4,991,582 A | 2/1991 | Byers et al. |
| 4,994,023 A | 2/1991 | Wellinghoff et al. |

(Continued)

FOREIGN PATENT DOCUMENTS

DE  197 16 683 C1  6/1998

(Continued)

OTHER PUBLICATIONS

Low, et al., "Microactuators Towards Microvalves for Responsive Controlled Drug Delivery," *Sensors & Actuators B* 67: 149-60 (2000).

(Continued)

*Primary Examiner* — Patricia Mallari
(74) *Attorney, Agent, or Firm* — Sutherland Asbill & Brennan LLP

(57) ABSTRACT

Medical devices, utilizing multiple reservoirs to protect and selectively expose sensors or other reservoir contents, are provided having (i) a reservoir contents destruction mechanism to interrupt the release or exposure of reservoir contents, for example, to deactivate an unneeded sensor and prevent it from negatively impacting other sensors, (ii) a protective covering material layer over the sensor underneath the reservoir cap, which protects the sensor membrane and sensor during reservoir cap disintegration and then is removed, (iii) a device design for containing sensors in shallow, wide reservoir structures to enhance sensor exposure by minimizing molecular diffusion distances, (iv) an implantable sensor unit and a separate drug delivery unit, or (v) combinations thereof.

28 Claims, 5 Drawing Sheets

U.S. PATENT DOCUMENTS

| | | |
|---|---|---|
| 5,041,107 A | 8/1991 | Heil, Jr. |
| 5,042,975 A | 8/1991 | Chien et al. |
| 5,147,297 A | 9/1992 | Myers et al. |
| 5,167,625 A | 12/1992 | Jacobsen et al. |
| 5,170,801 A | 12/1992 | Casper et al. |
| 5,196,002 A | 3/1993 | Hanover et al. |
| 5,200,051 A | 4/1993 | Cozzette et al. |
| 5,252,294 A | 10/1993 | Kroy et al. |
| 5,262,127 A | 11/1993 | Wise et al. |
| 5,279,607 A | 1/1994 | Schentag et al. |
| 5,304,293 A | 4/1994 | Tierney et al. |
| 5,318,557 A | 6/1994 | Gross |
| 5,324,316 A | 6/1994 | Schulman et al. |
| 5,336,213 A | 8/1994 | D'Angelo et al. |
| 5,366,454 A * | 11/1994 | Currie et al. ............... 604/890.1 |
| 5,368,588 A | 11/1994 | Bettinger |
| 5,368,704 A | 11/1994 | Madou et al. |
| 5,380,272 A | 1/1995 | Gross |
| 5,385,709 A | 1/1995 | Wise et al. |
| 5,391,250 A | 2/1995 | Cheney, II et al. |
| 5,405,367 A | 4/1995 | Schulman et al. |
| 5,427,585 A | 6/1995 | Bettinger |
| 5,443,508 A | 8/1995 | Giampapa |
| 5,474,527 A | 12/1995 | Bettinger |
| 5,493,177 A | 2/1996 | Muller et al. |
| 5,497,772 A | 3/1996 | Schulman et al. |
| 5,504,026 A | 4/1996 | Kung |
| 5,524,338 A | 6/1996 | Martyniuk et al. |
| 5,533,995 A | 7/1996 | Corish et al. |
| 5,569,186 A * | 10/1996 | Lord et al. ....................... 604/67 |
| 5,605,662 A | 2/1997 | Heller et al. |
| 5,651,767 A | 7/1997 | Schulman et al. |
| 5,660,163 A | 8/1997 | Schulman et al. |
| 5,662,689 A | 9/1997 | Elsberry et al. |
| 5,750,926 A | 5/1998 | Schulman et al. |
| 5,776,172 A | 7/1998 | Schulman et al. |
| 5,782,799 A | 7/1998 | Jacobsen et al. |
| 5,782,891 A | 7/1998 | Hassler et al. |
| 5,791,344 A | 8/1998 | Schulman et al. |
| 5,797,898 A | 8/1998 | Santini, Jr. et al. |
| 5,824,204 A | 10/1998 | Jerman |
| 5,843,767 A | 12/1998 | Beattie |
| 5,882,494 A | 3/1999 | Van Antwerp |
| 5,893,974 A | 4/1999 | Keller et al. |
| 5,917,346 A | 6/1999 | Gord |
| 5,938,691 A | 8/1999 | Schulman et al. |
| 5,938,923 A | 8/1999 | Tu et al. |
| 5,949,187 A | 9/1999 | Xu et al. |
| 5,957,958 A | 9/1999 | Schulman et al. |
| 5,962,081 A | 10/1999 | Ohman et al. |
| 5,971,931 A | 10/1999 | Raff |
| 5,976,101 A | 11/1999 | Sibalis |
| 5,976,336 A | 11/1999 | Dubrow et al. |
| 5,989,445 A | 11/1999 | Wise et al. |
| 5,999,848 A | 12/1999 | Gord et al. |
| 5,999,849 A | 12/1999 | Gord et al. |
| 6,001,090 A | 12/1999 | Lenhart |
| 6,042,710 A | 3/2000 | Dubrow |
| 6,043,437 A | 3/2000 | Schulman et al. |
| 6,047,214 A | 4/2000 | Mueller et al. |
| 6,051,017 A | 4/2000 | Loeb et al. |
| 6,066,163 A | 5/2000 | John |
| 6,067,474 A | 5/2000 | Schulman et al. |
| 6,071,391 A * | 6/2000 | Gotoh et al. ............. 204/403.05 |
| 6,081,736 A | 6/2000 | Colvin et al. |
| 6,114,658 A | 9/2000 | Roth et al. |
| 6,119,028 A | 9/2000 | Schulman et al. |
| 6,123,861 A | 9/2000 | Santini, Jr. et al. |
| 6,129,685 A | 10/2000 | Howard, III |
| 6,161,047 A | 12/2000 | King et al. |
| 6,171,850 B1 | 1/2001 | Nagle et al. |
| 6,178,349 B1 | 1/2001 | Kieval |
| 6,185,452 B1 | 2/2001 | Schulman et al. |
| 6,185,455 B1 | 2/2001 | Loeb et al. |
| 6,214,032 B1 | 4/2001 | Loeb et al. |
| 6,232,150 B1 | 5/2001 | Lin et al. |
| 6,259,937 B1 | 7/2001 | Schulman et al. |
| 6,261,584 B1 | 7/2001 | Peery et al. |
| 6,264,990 B1 | 7/2001 | Knepp et al. |
| 6,289,237 B1 | 9/2001 | Mickle et al. |
| 6,306,420 B1 | 10/2001 | Cheikh |
| 6,319,241 B1 | 11/2001 | King et al. |
| 6,328,699 B1 | 12/2001 | Eigler et al. |
| 6,334,859 B1 | 1/2002 | Richter |
| 6,340,421 B1 | 1/2002 | Vachon et al. |
| 6,349,232 B1 | 2/2002 | Gordon |
| 6,384,353 B1 | 5/2002 | Huang et al. |
| 6,387,048 B1 | 5/2002 | Schulman et al. |
| 6,413,393 B1 | 7/2002 | Van Antwerp et al. |
| 6,436,853 B2 | 8/2002 | Lin et al. |
| 6,462,162 B2 | 10/2002 | Van Antwerp et al. |
| 6,472,122 B1 | 10/2002 | Schulman et al. |
| 6,477,395 B2 | 11/2002 | Schulman et al. |
| 6,480,730 B2 | 11/2002 | Darrow et al. |
| 6,483,368 B2 | 11/2002 | Mayer et al. |
| 6,484,045 B1 | 11/2002 | Holker et al. |
| 6,491,666 B1 | 12/2002 | Santini, Jr. et al. |
| 6,498,043 B1 | 12/2002 | Schulman et al. |
| 6,512,939 B1 | 1/2003 | Colvin et al. |
| 6,516,808 B2 | 2/2003 | Schulman |
| 6,520,326 B2 | 2/2003 | McIvor et al. |
| 6,520,936 B1 | 2/2003 | Mann |
| 6,527,762 B1 | 3/2003 | Santini, Jr. et al. |
| 6,533,798 B2 | 3/2003 | Greenberg et al. |
| 6,537,250 B1 | 3/2003 | Kriesel |
| 6,537,256 B2 | 3/2003 | Santini, Jr. et al. |
| 6,551,838 B2 | 4/2003 | Santini, Jr. et al. |
| 6,564,807 B1 | 5/2003 | Schulman et al. |
| 6,571,125 B2 | 5/2003 | Thompson |
| 6,572,531 B2 | 6/2003 | Zilberman et al. |
| 6,587,719 B1 | 7/2003 | Barrett et al. |
| 6,656,162 B2 | 12/2003 | Santini, Jr. et al. |
| 6,663,615 B1 | 12/2003 | Madou et al. |
| 6,669,683 B2 | 12/2003 | Santini, Jr. et al. |
| 6,730,072 B2 | 5/2004 | Shawgo et al. |
| 6,733,485 B1 | 5/2004 | Whitehurst et al. |
| 6,757,560 B1 | 6/2004 | Fischer et al. |
| 6,773,429 B2 | 8/2004 | Sheppard, Jr. et al. |
| 6,808,522 B2 | 10/2004 | Richards et al. |
| 6,827,250 B2 | 12/2004 | Uhland et al. |
| 6,849,463 B2 | 2/2005 | Santini, Jr. et al. |
| 6,908,770 B1 | 6/2005 | McDevitt et al. |
| 6,968,743 B2 | 11/2005 | Rich et al. |
| 7,010,345 B2 | 3/2006 | Hill et al. |
| 2001/0053885 A1 | 12/2001 | Gielen et al. |
| 2002/0022826 A1 | 2/2002 | Reynolds et al. |
| 2002/0038137 A1 | 3/2002 | Stein |
| 2002/0055761 A1 | 5/2002 | Mann et al. |
| 2002/0072734 A1 | 6/2002 | Liedtke |
| 2002/0072784 A1 | 6/2002 | Sheppard, Jr. et al. |
| 2002/0082665 A1 | 6/2002 | Haller et al. |
| 2002/0099359 A1 | 7/2002 | Santini, Jr. et al. |
| 2002/0107553 A1 | 8/2002 | Hill et al. |
| 2002/0111601 A1 | 8/2002 | Thompson |
| 2002/0111658 A1 | 8/2002 | Greenberg et al. |
| 2002/0120186 A1 * | 8/2002 | Keimel ........................ 600/365 |
| 2002/0143369 A1 | 10/2002 | Hill et al. |
| 2002/0144548 A1 | 10/2002 | Cohn et al. |
| 2002/0165586 A1 | 11/2002 | Hill et al. |
| 2002/0183721 A1 | 12/2002 | Santini, Jr. et al. |
| 2002/0187260 A1 | 12/2002 | Sheppard, Jr. et al. |
| 2003/0004549 A1 | 1/2003 | Hill et al. |
| 2003/0032946 A1 | 2/2003 | Fishman |
| 2003/0049865 A1 | 3/2003 | Santini, Jr. et al. |
| 2003/0055344 A1 | 3/2003 | Eigler et al. |
| 2003/0069560 A1 | 4/2003 | Adamis et al. |
| 2003/0178403 A1 | 9/2003 | Lemmerhirt et al. |
| 2004/0043042 A1 | 3/2004 | Johnson et al. |
| 2004/0082937 A1 | 4/2004 | Ausiello et al. |
| 2004/0106914 A1 | 6/2004 | Coppeta et al. |
| 2004/0106953 A1 | 6/2004 | Yomtov et al. |
| 2004/0121486 A1 | 6/2004 | Uhland et al. |
| 2004/0127942 A1 | 7/2004 | Yomtov et al. |
| 2004/0166140 A1 | 8/2004 | Santini, Jr. et al. |
| 2004/0247671 A1 | 12/2004 | Prescott et al. |
| 2004/0248320 A1 | 12/2004 | Santini, Jr. et al. |
| 2005/0050859 A1 | 3/2005 | Coppeta et al. |

| 2005/0055014 A1 | 3/2005 | Coppeta et al. |
| 2005/0100937 A1 | 5/2005 | Holmes |
| 2006/0004272 A1 | 1/2006 | Shah et al. |

FOREIGN PATENT DOCUMENTS

| WO | WO 02/056862 A1 | 7/2002 |

OTHER PUBLICATIONS

Madou, et al., "From Batch to Continuous Manufacturing of Microbiomedical Devices," *Chem Rev.* 100: 2679-92 (2000).
Madou, et al., "Exploitation of a Novel Artificial Muscle for Controlled Drug Delivery," *Polym. Mater. Sci. Eng.* 83: 495-497 (2000).
Santini, et al., *Angew Chem. Int. Ed. Engl.* 39(14): 2396-407 (2000).
Santini, et al., *Ann. Med.* 32(6) 377-79 (2001) (abstract).
Santini, et al., *Nature* 397(6717): 335-38 (1999).
Surbled, et al., "Shape Memory Alloys for Micromembranes Actuation," *SPIE* 3825: 63-70 (1999).
Surbled, et al., "Array of Shape Memory Alloy One-Shot Micro-Valves for Drug Delivery", MME '99, Gif sur Yvette, France (Sep. 27-28, 1999).
Surbled, et al., *Jpn. J. Applied Phys.* 38: L1547-49 (1999).
Tao, et al., *Adv. Drug Deliv. Res.* 55(3): 315-28 (2003).
Tierney, et al., "Electroreleasing Composite Membranes for Delivery of Insulin and Other Biomacromolecules," *J. Electrochem Soc.* 137(6): 2005-06 (1990).
Tierney, et al., "New Electrorelease Systems Based on Microporous Membranes," *J. Electrochem Soc.* 137(12): 3789-93 (1990).
Patzer, et al. "A Microchip Glucose Sensor", *Asaio Journal*, 41(3): 409-413 (Jul. 1, 1995).

* cited by examiner

MEDICAL DEVICE FOR SENSING GLUCOSE

CROSS-REFERENCE TO RELATED APPLICATIONS

This application claims the benefit of U.S. Provisional Application No. 60/516,865, filed Nov. 3, 2003, and U.S. Provisional Application No. 60/577,720, filed Jun. 7, 2004. These applications are incorporated herein by reference in their entirety.

BACKGROUND OF THE INVENTION

This invention is in the field of miniaturized devices having reservoirs for storage and protection of subdevices, subcomponents, and/or diagnostic reagents and other chemicals, with means for selectively releasing or exposing the subdevices, subcomponents, and/or chemicals, particularly in the field of medical devices for diagnostic sensing.

U.S. Pat. Nos. 5,797,898 and 6,551,838 to Santini, et al., which are incorporated herein by reference, describe devices that release chemical molecules from, or expose sensors located in, reservoirs using controlled release and exposure mechanisms. The devices can be used in initiating and controlling chemical reactions, analyses, or measurements in a micro-scale area or volume, continuously or at specific points in time. In some of the devices, the reservoir-opening mechanism utilizes a reservoir cap covering a reservoir that is selectively disintegrated to open the reservoir and permit the reservoir contents to be released or exposed to the environment outside of the device.

In some instances, however, it would be desirable to interrupt the release or exposure after the reservoir has been opened. For example, a device may have an array (e.g., tens or hundreds) of closely spaced reservoirs, each of which contain a glucose oxidase-based sensor. After a period of operation using a first sensor, the sensor typically will become increasingly inaccurate. Therefore, a second reservoir is opened to newly expose a second sensor for use. The first sensor, however, may continue to produce peroxide even after it is no longer being used. The peroxide could diffuse to the second sensor and confound the glucose reading. Furthermore, the glucose oxidase-catalyzed reaction also will consume oxygen locally. More generally, the catalytic activity of an enzyme contained within the first sensor (first reservoir) may perturb the concentration of reactants such as oxygen or products such as peroxide in the vicinity of the second sensor. Therefore, it would be desirable to stop the release of peroxide from the first reservoir after the first sensor is no longer useful. Similarly, it would be desirable to selectively interrupt the release or exposure of other reservoir contents.

SUMMARY OF THE INVENTION

Improved medical devices, such as implantable sensors, are provided.

In one aspect, a device is provided for the controlled exposure of a secondary device and includes means for selectively deactivating or rendering inoperable the secondary device, such as when the secondary device no longer works properly. In one embodiment, the device comprises a substrate; a plurality of reservoirs (e.g., microreservoirs) in the substrate; an operational secondary device in one or more of the reservoirs; a reservoir cap covering each of the reservoirs to isolate the secondary device from an environmental component outside the reservoirs, wherein the reservoir cap is impermeable to the environmental component; means for disintegrating or permeabilizing the reservoir cap to expose the secondary device to the environmental component; and means for selectively rendering the secondary device inoperable. The substrate can comprise two or more portions, for example, bonded together, or the substrate can be monolithic.

In preferred embodiments, the secondary device comprises a sensor or a sensing component. In one embodiment, the sensor or sensing component comprises a glucose sensor. For example, the sensor or sensor component can comprise glucose oxidase. In one particular embodiment, the sensor comprises at least one working electrode, a counter electrode, an enzyme provided on the at least one working electrode, and a semipermeable membrane covering the enzyme and at least part of the at least one working electrode.

Various means are provided for selectively rendering the secondary device inoperable. In one embodiment, the means for selectively rendering the secondary device inoperable comprises a thermal ablation electrode, which renders the operational secondary device inoperable upon passage of an electric current therethrough. In another embodiment, the means for selectively rendering the secondary device inoperable comprises a resistive heater. In one specific embodiment, the sensor or sensor component comprises an enzyme, such as glucose oxidase for example, and the resistive heater generates heat effective to deactivate the enzyme. In other embodiments, the means for selectively rendering the secondary device inoperable comprises one or more chemical reactant materials that react to generate energy, an expanding gas, or other reaction product to render the operational secondary device inoperable.

In various embodiments, the means for disintegrating or permeablizing the reservoir cap comprises a microprocessor programmed to initiate the disintegrating or permeabilizing at a specified time, upon receipt of a signal from another device, or upon detection of a specified sensed condition.

In one embodiment, the device further comprises a biodegradable intermediary material disposed in the reservoir underneath the reservoir cap and covering the secondary device. In another embodiment, the device further includes a thin layer of a structural material underneath the reservoir cap and an evacuated or gas-filled space in the reservoir between the secondary device and the structural material layer. In still another embodiment, the device is part of an implantable sensor unit, which is part of a medical device that also includes a drug delivery unit comprising at least one therapeutic agent for release, wherein the drug delivery unit is in communication with the implantable sensor unit and releases the therapeutic agent in response to the sensor's sensing of the environmental component.

In another aspect, a device is provided for the controlled exposure of a secondary device and includes means for protecting the secondary device during the reservoir opening step. In one embodiment, the device comprises a substrate; a plurality of reservoirs (e.g., microreservoirs) in the substrate; a secondary device in one or more of the reservoirs; a reservoir cap covering each of the reservoirs to isolate the secondary device from an environmental component outside the reservoirs, wherein the reservoir cap is impermeable to the environmental component; a biodegradable intermediary material disposed in the reservoir underneath the reservoir cap and covering the secondary device; and means for disintegrating or permeabilizing the reservoir cap to expose the biodegradable intermediary material to a fluid from outside the device to cause the biodegradable intermediary material to disintegrate to expose the secondary device to the environmental component. In one embodiment, the device further includes a layer of a structural material, such as a dielectric, underneath the reservoir cap and disposed between the biodegradable intermediary material and the reservoir cap. In one embodiment, the biodegradable intermediary material comprises a water-soluble solid, liquid, or gel. In another embodiment, the biodegradable intermediary material comprises a polyethylene glycol, a polyethylene oxide, or a copolymer of poly(lactic-co-glycolic) acid.

In another embodiment, a device is provided for the controlled exposure of a secondary device, which comprises: a substrate; a plurality of reservoirs (e.g., microreservoirs) in the substrate; a secondary device in one or more of the reservoirs; a reservoir cap covering each of the reservoirs to isolate the secondary device from an environmental component outside the reservoirs, wherein the reservoir cap is impermeable to the environmental component; an evacuated or gas-filled space disposed in the reservoir between the reservoir cap and the secondary device; and means for disintegrating or permeabilizing the reservoir cap to expose the secondary device to the environmental component.

In another aspect, a method is provided for making a device for the controlled exposure of a secondary device comprising the steps of: (a) providing a substrate having a secondary device which is disposed in a reservoir in the substrate; (b) depositing a water-soluble material in the reservoir over the secondary device; (c) depositing a reservoir cap material over the water-soluble material; (d) contacting the water-soluble material with an aqueous solvent to dissolve the water-soluble material; (e) removing the water soluble material and solvent from the reservoir through one or more apertures to form an open space in the reservoir in place of the deposited water soluble material; and (f) plugging the one or more apertures. In one embodiment, the method further includes depositing a layer of a structural material, such as a dielectric material for example, over the water-soluble material before the step of depositing the reservoir cap material. In another embodiment, the method further includes etching one or more apertures through the structural material layer. In one embodiment, the method includes depositing a reservoir cap material over the structural material layer. In one embodiment, the step of plugging the apertures can comprise filling the apertures with the reservoir cap material, and in another embodiment the apertures are filled with a polymeric material.

In another aspect, methods are provided for detecting or measuring a property at a site, the method comprising the steps of: placing at the site one of the reservoir devices described herein; then disintegrating or permeabilizing the reservoir cap to expose the sensor or sensing component in one of the reservoirs; and then detecting or measuring a property in or adjacent to the exposed sensor or sensor component. In one embodiment, the method further comprises rendering the sensor or sensor component inoperable. For example, the sensor or sensor component can be rendered inoperable by passing an electric current through a fuse or resistive heater which is positioned proximate the sensor or sensing component.

In another aspect, a medical apparatus is provided for both sensing and drug delivery. In a preferred embodiment, the apparatus comprises: (a) at least one implantable sensor unit which comprises: a plurality of reservoirs, a sensor or sensor component provided in the reservoirs, a reservoir cap covering the reservoirs to isolate the sensor from an environmental component outside the reservoirs, wherein the reservoir cap is impermeable to the environmental component, and a means for disintegrating or permeabilizing the reservoir cap to expose the sensor to the environmental component; and (b) at least one drug delivery unit which comprises at least one therapeutic agent for delivery to a patient, wherein the drug delivery unit is in communication with the implantable sensor unit and releases the therapeutic agent in response to the sensor's sensing of the environmental component. For example, the sensor can measure a patient's glucose level and the drug delivery unit can release insulin.

In one embodiment, the drug delivery unit communicates with the sensor unit via at least one flexible conductor connecting the units. For example, the flexible conductor can include a connector means for separating and connecting together the units. The communication between the drug delivery unit and the implantable sensor unit can comprise, for example, transmission of a digital or analog signal. In other embodiments, the communication between the drug delivery unit and the implantable sensor unit can comprise transmission of light, electromagnetic energy, sonic energy, hydraulic energy, or a combination thereof. In various embodiments, the communication between the drug delivery unit and the implantable sensor unit comprises a conductor, such as one or more wires, optical fibers, fluid-filled lumens, or combinations thereof. In another embodiment, the communication between the drug delivery unit and the implantable sensor unit is without a conductor physically connecting the two units. For example, the apparatus can further include one of more signal encoders/transducers, emitters, receivers, decoders/transducers, or combinations thereof.

In one embodiment, the drug delivery unit is implantable, and in an alternative embodiment, the drug delivery unit is adapted to be worn externally by a patient. For example, the drug delivery unit can include an implantable or external pump for pumping the therapeutic agent into the patient. In one embodiment, the drug delivery unit comprises: a substrate; a plurality of reservoirs in the substrate; at least one therapeutic agent in one or more of the reservoirs; reservoir caps covering the reservoirs to isolate the therapeutic agent inside the reservoirs; and means for disintegrating or permeabilizing one or more of the reservoir caps to release the therapeutic agent from one or more of the reservoirs.

DETAILED DESCRIPTION OF THE INVENTION

Figure 1:
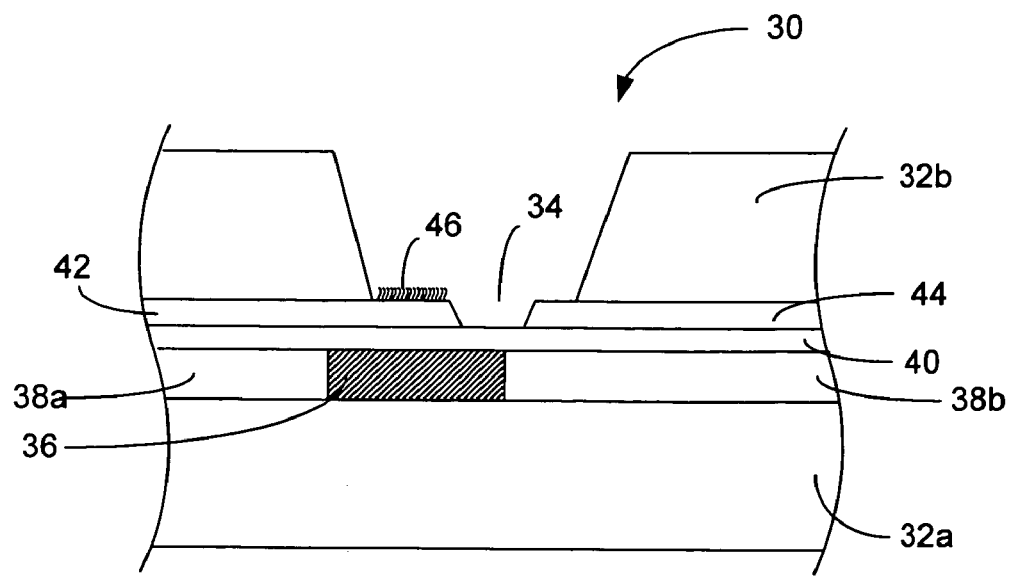
FIG. 1 is a cross-sectional view of one embodiment of a reservoir device for destroying or deactivating reservoir contents by a thermal or electrothermal mechanism.

Improved multi-reservoir devices, and methods of manufacture and use thereof, have been developed. Preferably, the devices and methods comprise implantable sensors, such as for use in in vivo sensing, e.g., of glucose, in a human or other animal. The devices and methods optionally can further comprise drug delivery means in communication with the sensors.

The devices described herein includes a plurality of reservoirs containing reservoir contents (such as a sensor or reactant), where each reservoir is covered by a selectively removable reservoir cap (i.e., a barrier layer) that protects the reservoir contents from one or more components of the surrounding environment until such time as exposure or release is desired. Examples of these environmental components include chemicals, cells, proteins, water, air or other gases, biological fluids and constituents thereof, as well as certain forms of energy, such as light or heat.

The improvements include (1) a reservoir contents destruction mechanism to interrupt the release or exposure of reservoir contents, for example, to deactivate an unneeded sensor and prevent it from negatively impacting other (nearby) sensors, (2) a protective covering material layer over the sensor underneath the reservoir cap, which protects the sensor membrane and sensor during reservoir cap disintegration and then is removed, (3) a device design for containing sensors in shallow, wide reservoir structures to enhance sensor exposure by minimizing molecular diffusion distances, (4) a device having an implantable sensor unit and a separate drug delivery unit, and (5) combinations thereof.

In one aspect, an implantable medical device is provided for the controlled exposure of a secondary device, particularly a sensor, such as a glucose sensor. In one embodiment, the device includes at least one substrate, a plurality of reservoirs in the substrate, an operational secondary device in one or more of the reservoirs, a reservoir cap covering each of the reservoirs to isolate the secondary device from an environmental component outside the reservoirs wherein the reservoir is impermeable to the environmental component, means for disintegrating or permeabilizing the reservoir cap to expose the secondary device to the environmental component; and means for selectively rendering the secondary device inoperable. In another embodiment, the device includes at least one substrate, a plurality of reservoirs in the substrate, a secondary device in one or more of the reservoirs, a reservoir cap covering each of the reservoirs to isolate the secondary device from an environmental component outside the reservoirs wherein the reservoir is impermeable to the environmental component, a biodegradable intermediary material disposed in the reservoir underneath the reservoir cap and covering the secondary device, and means for disintegrating or permeabilizing the reservoir cap to expose the biodegradable intermediary material to cause the biodegradable intermediary material to disintegrate to expose the secondary device to the environmental component. In a preferred embodiment, the biodegradable intermediary material is water miscible, such as a water-soluble solid, liquid, or gel, a hydrophilic polymer matrix (e.g., a hydrogel), or a liquid that readily mixes with an aqueous fluid. The liquid mixture should permit an analyte (such as glucose) to diffuse through it to reach a sensor thereunder.

In another aspect, a medical device is provided that includes an implantable sensor portion (or sensor unit) and a separate drug delivery portion (or drug unit). The drug delivery portion can be implantable or designed to be worn externally. The sensor portion and the drug delivery portion operate together to sense in vivo a chemical entity or physiological condition and deliver one or more drugs as therapeutically indicated, based at least in part on a signal from the sensor portion.

As used herein, the terms "comprise," "comprising," "include," and "including" are intended to be open, non-limiting terms, unless the contrary is expressly indicated.

ILLUSTRATIVE EMBODIMENTS

Sensor Devices with Deactivation Mechanism

In one embodiment, the sensor or reservoir contents are destroyed by a thermal or electrothermal ablation mechanism. Electrothermal ablation, as described in U.S. patent application Publication No. 2004/0121486 A1, includes passing electric current through a conductive structure to locally heat it in an amount effective to "rupture" it, e.g., an electrically-induced thermal shock that causes the structure to fracture and/or lose structural integrity due to a phase change, (e.g., melting or vaporization), either or both of which are caused by the generation of heat within the structure as a result of electric current flowing through it. While not being bound to any theory, the heating is believed to cause the structure to degrade by melting (or vaporizing), thermal shock, and/or a mismatch in the coefficient of thermal expansion, analogous to the process by which a conventional simple electrical fuse heats and then disintegrates (e.g., burns up) upon passage of an excessive amount of electrical current through it.). This rupturable structure is sometimes referred to herein as a "fuse."

In one embodiment, the means for selectively rendering the secondary device inoperable comprises an electrothermal ablation-based destruction mechanism. In one preferred embodiment, a fuse is provided beneath a glucose oxidase-based sensor in a reservoir, as shown in FIG. 1. For simplicity, FIG. 1 shows a single, opened reservoir, although the device 30 would include a plurality of reservoirs, each of which would be sealed with a reservoir cap prior to actuation of the reservoir. Device 30 includes a substrate consisting of a lower substrate portion 32*a* and an upper substrate portion 32*b* in which reservoir 34 is disposed. A sensor is provided in the reservoir and includes working electrode 42, counter electrode 44, and glucose oxidase 46. The device 30 further includes a sensor deactivation mechanism, which includes fuse 36 and fuse traces 38*a* and 38*b*. An insulating dielectric layer 40 separates the working and counter electrodes 42, 44 from the fuse and fuse traces 36, 38. When the sensor is no longer needed, the fuse 36 is blown, thus destroying the sensor. Residual active glucose oxidase may remain.

Figure 2:
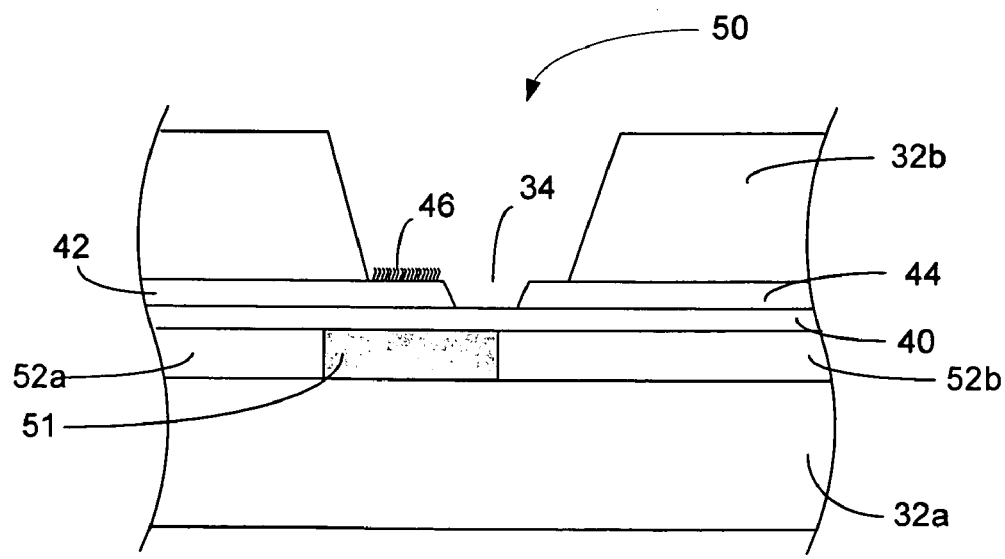
FIG. 2 is a cross-sectional view of another embodiment of a reservoir device for destroying or deactivating reservoir contents by a thermal or electrothermal mechanism.

In another embodiment, the means for selectively rendering the secondary device inoperable comprises a thermal destruction mechanism based on conventional resistive heating. In another preferred embodiment, a resistor is provided beneath a glucose oxidase-based sensor in a reservoir, as shown in FIG. 2, which for simplicity also shows a single, opened reservoir, although the device 50 would include a plurality of reservoirs, each of which would be sealed with a reservoir cap prior to actuation of the reservoir. Device 50 includes a substrate consisting of a lower substrate portion 32*a* and an upper substrate portion 32*b* in which reservoir 34 is disposed. A sensor is provided in the reservoir and includes working electrode 42, counter electrode 44, and glucose oxidase 46. The device 50 further includes a sensor deactivation mechanism, which includes resistor 51 and current traces 52*a* and 52*b*. A thin insulating dielectric layer 40 separates the working and counter electrodes 42, 44 from the resistor and current traces 51, 52. When the sensor is no longer needed, an electric current is passed through the resistor 51, heating the glucose oxidase to a temperature effective to deactivate the enzyme. This will eliminate the possibility of residual peroxide formation and resulting sensor crosstalk. Typically but not necessarily, the "render inoperable" step would be used after the sensor or sensor component has been exposed and used to detect or measure.

While only one reservoir/sensor is shown in FIGS. 1 and 2, a medical device comprising device 30 or device 50, respectively, preferably comprises an array of tens or hundreds of such reservoirs/sensors. In addition, while not shown, the enzyme 46 optionally and preferably would be covered by a selectively porous membrane as known in the art to control the diffusion of glucose and/or other molecules to the enzyme. See, for example, U.S. Pat. No. 4,759,828, which is incorporated herein by reference. Furthermore, while not shown, the medical devices preferably include reservoir caps and mechanisms for selectively disintegrating or permeabilizing the reservoir caps to open the reservoir and expose the sensor therein, so that the glucose sensors are protected from the surrounding environment until it is desired to expose them. Examples of useful active reservoir cap opening mechanisms are described in U.S. Pat. Nos. 5,797,898; 6,527,762; 6,491,666; and 6,551,838; and U.S. patent application Publication No. 2004/0121486 to Uhland, et al., which are incorporated herein by reference.

In still other embodiments, the means for selectively rendering the secondary device inoperable involves a chemical reaction mechanism. For example, a chemical reaction could be initiated beneath the sensor, to produce energy, an expanding gas, or a reaction product that chemically deactivates the sensor.

In another embodiment (not shown), a single reservoir contains more than one sensor. For example, two sensors could be provided in a side-by-side arrangement, for instance in a relatively larger reservoir. These could work in parallel, e.g., to provide two signals simultaneously, or they could be redundant, e.g., where the second one is used when/if the first one fails.

Sensor Device With Protective Covering

In another aspect, a protective covering material is provided over the sensor in the reservoir, underneath the reservoir cap. The protective covering material protects the sensor membrane and sensor during reservoir cap disintegration, e.g., by an electrothermal ablation mechanism. Once the reservoir cap is opened, the protective covering material is removed by the body or is otherwise displaced to expose the functional sensor for operation. For example, the protective covering dissolves into the body so that the sensor can contact one or more environmental components (e.g., analytes, proteins, antibodies, and the like) or forces (e.g., pressure). Examples of the protective covering include biocompatible gases and biodegradable solids and liquids.

In one embodiment, the protective covering is a biodegradable intermediary material. As used herein, the term "biodegradable intermediary material" refers to a solid, liquid, or gel material that is water miscible or that is dissolved, chemically or physically degraded, and/or adsorbed by the body of a patient in vivo. In a preferred embodiment, the biodegradable intermediary material is water miscible, such as a water-soluble solid, liquid, or gel, a hydrophilic polymer matrix (e.g., a hydrogel), or a liquid that readily mixes with an aqueous fluid. The liquid mixture should permit an analyte (such as glucose) to diffuse through it to reach a sensor thereunder. Examples of suitable water-soluble materials include biocompatible polymers, such as a polyethylene glycol (PEG) or a polyethylene oxide (PEO). In alternative embodiments, the material is a bioerodible or biodegradable polymer, such as a copolymer of poly(lactic-co-glycolic) acid (PLGA), rather than a water-soluble polymer. The biodegradable intermediary material can be in a porous form to enhance the dissolution or disintegration kinetics.

In another embodiment, the protective covering is an evacuated or gas-filled space. Examples of gases include air, oxygen, nitrogen, helium, or argon. It may be particularly desirable to include a gaseous layer beneath the reservoir caps that open by electrothermal ablation, because such a configuration could increase the efficiency of the opening mechanism. For instance, if the reservoir cap is in contact with a medium that allows heat to easily pass away (e.g., a solid or liquid having high thermal conductivity), then it would require more electric current to electrothermally ablate the reservoir cap than would be required if the reservoir cap is in contact with a gas or other good thermal insulator. Thus, by using air as the protective layer, less electric current must be passed through the reservoir cap to heat it to the point of failure, i.e., to electrothermally ablate it or "blow the fuse."

Figure 4:
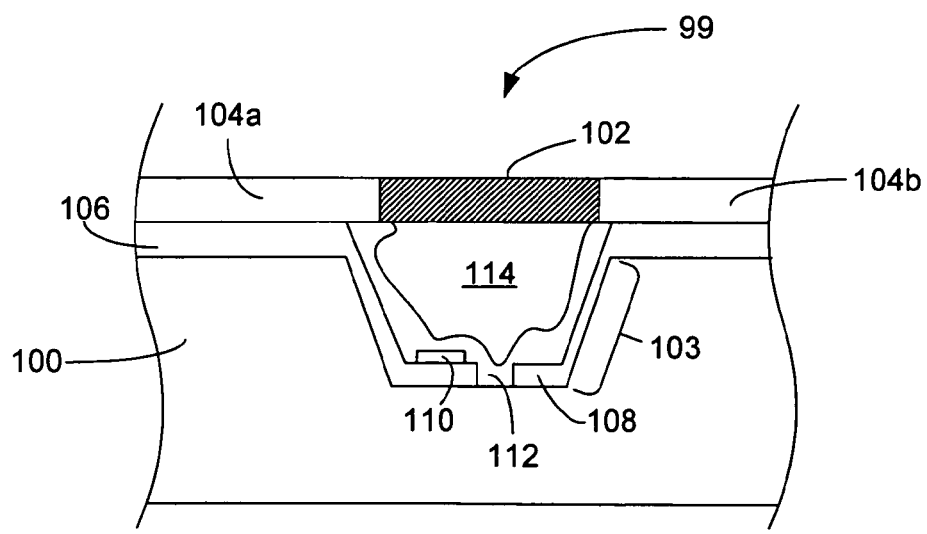
FIG. 4 is a cross-sectional view of one embodiment of a multi-reservoir sensor device having a water-soluble material disposed between the sensor membrane and a reservoir cap.

One preferred embodiment is illustrated in FIG. 4. Device 99 (which for example would be part of an implantable medical device) includes substrate 100 having reservoir 103, which contains a sensor which includes working electrode 106, counter electrode 108, enzyme 110, and sensor membrane 112. The reservoir is covered by reservoir cap 102, which is connected to electric traces 104*a* and 104*b*. A water-soluble material 114 is provided as a protective covering between the reservoir cap and the sensor. Optionally, device 99 could further include a sensor-deactivation mechanism (not shown) built underneath the sensor in/on the substrate.

Figure 5:
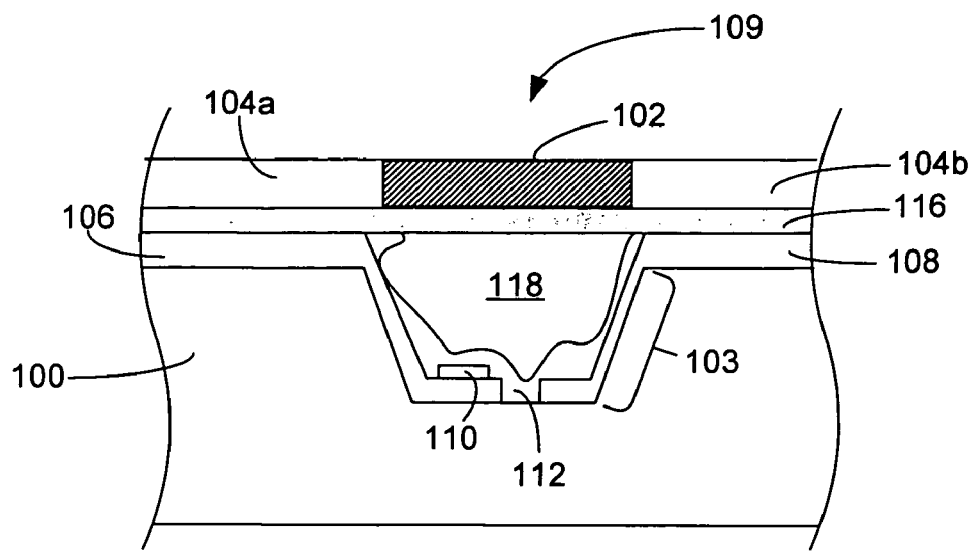
FIG. 5 is a cross-sectional view of another embodiment of a multi-reservoir sensor device having a hollow cavity between the sensor membrane and a reservoir cap.

Another preferred embodiment is shown in FIG. 5. Device 109 (which for example would be part of an implantable medical device) includes substrate 100 having reservoir 103, which contains a sensor which includes working electrode 106, counter electrode 108, enzyme 110, and sensor membrane 112. The reservoir is covered by reservoir cap 102, which is connected to electric traces 104*a* and 104*b*. A hollow cavity 118 is provided over the sensor membrane, and underneath a thin dielectric or other structural layer 116. Optionally, device 109 could further include a sensor-deactivation mechanism (not shown) built underneath the sensor in/on the substrate. The dielectric and hollow cavity protect the sensor membrane and sensor during reservoir cap disintegration. When the reservoir cap is disintegrated (e.g., by electrothermal ablation), the dielectric/structural layer is also destroyed, exposing the functional sensor for operation.

The hollow cavity of device 109 could be made in a number of different fabrication approaches. In one embodiment, a soluble material, such as a water-soluble polymer, is deposited over the sensor membrane, and then the thin dielectric material layer or other structural layer is deposited over the soluble material. Next, small holes or slats are etched through the structural layer over the water-soluble material, and then the structure is then soaked in a solvent, e.g., water, to cause the soluble material to dissolve out, leaving in its place a hollow cavity. The technique of dissolving a sacrificial layer, such as a water-soluble material, to form a cavity is well known in the art of microfabrication. (University of Michigan researchers in the MEMS neural probe work published several papers demonstrating this concept, where silicon was dissolved to form fluidic channels.) This hollow cavity optionally may be filled with a fluid, such as a gas or liquid. The holes or slats are small enough that the reservoir cap can be deposited over them, or a polymeric material can be used to plug the holes or slats prior to deposition of the reservoir cap.

Sensor Device With Sensor/Reservoir On Substrate

FIGS. 1-5 show the sensor layer being located inside (and near the bottom of) a relatively deep reservoir. In some embodiments, however, it would be more preferable for (1) the reservoir to be shallow such that there is little to no distance between the surface of the sensor and the outer surface of the substrate, and/or (2) the sensor layer to be positioned on a substrate, such that there is no unfilled or empty space between the reservoir cap and the sensor layer. This would enhance diffusional mass transfer (of, for example, glucose or other analytes) by, for example, decreasing the distance molecules are required to diffuse into the reservoir and into contact with the sensor.

In one embodiment, the sensor device is built up layer by layer, instead of by bonding two substrates together. Thus, the "reservoir" is the space below the reservoir cap that contains the sensor materials, including the electrodes, enzyme, and polymeric membrane. In such a case, it is possible that the area denominated as the "reservoir" might actually be spatially located "above" that which typically is referred to as the substrate, in that the bottom of the sensor may be fabricated on the top surface of the substrate. In such instances, the term "reservoir" includes embodiments where the sensor is located in a defined space beneath the reservoir cap, and the term "substrate" includes the bottom substrate and other structural material layers built up thereon and around the sensor. Examples of such embodiments are illustrated in FIGS. 7-9.

Figure 7:
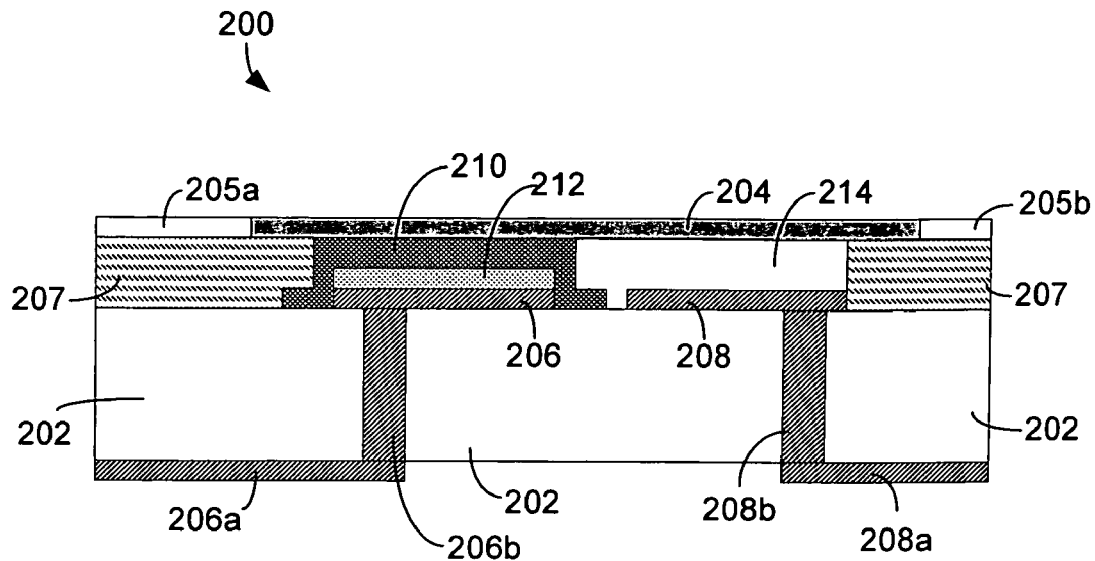
FIG. 7 is a cross-sectional view of one embodiment of sensor device with the sensor electrodes disposed in a reservoir covered by a disintegratable reservoir cap, where the working electrode and counter electrode extend through vias in the substrate for electrical connection.

FIG. 7 shows device 200, which includes substrate 202 and a reservoir defined within a reservoir cap 204 and a structural material 207. The reservoir contains a sensor comprising working electrode 206, counter electrode 208, semi permeable sensor membrane 210, sensor chemical component 212, and space 214. For example, the chemical component could be glucose oxidase mixed with a binder material. The space could be empty or filled, for example, with a gas or water-soluble material. The working electrode 206 and counter electrode 208 are electrically connected to other device electronics through vias 206b, 208b and electrical traces 206a, 208a. In operation, electric current is passed through the reservoir cap 204 through input and out leads 205a and 205b to electrothermally ablate the reservoir cap, disintegrating it and exposing the sensor therebeneath. In this embodiment, there is no gap or space between the reservoir cap 204 and the sensor membrane 210.

Figure 8:
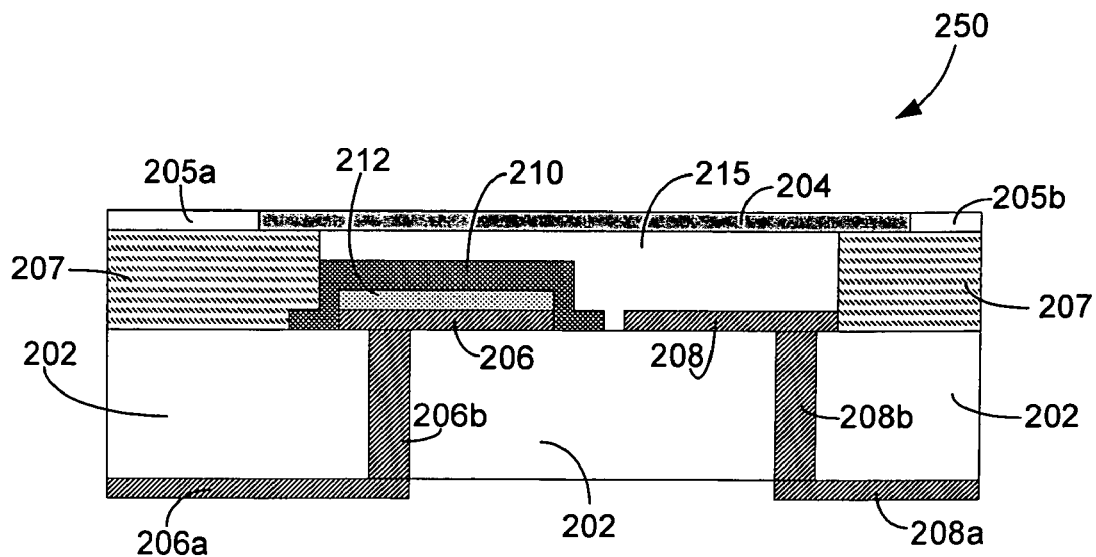
FIG. 8 is a cross-sectional view of another embodiment of sensor device with the sensor electrodes disposed in a reservoir covered by a disintegratable reservoir cap, where the working electrode and counter electrode extend through vias in the substrate for electrical connection.

Another variation of the device is shown in FIG. 8. Device 250 includes substrate 202 and a reservoir defined within a reservoir cap 204 and a structural material 207. The reservoir contains a sensor comprising working electrode 206, counter electrode 208, semi permeable sensor membrane 210, sensor chemical component 212, and space 215. The working electrode 206 and counter electrode 208 are electrically connected to other device electronics through vias 206b, 208b and electrical traces 206a, 208a. In operation, electric current is passed through the reservoir cap 204 through input and out leads 205a and 205b to electrothermally ablate the reservoir cap, disintegrating it and exposing the sensor therebeneath. In this embodiment, space 215 extends between the reservoir cap 204 and the sensor membrane 210. The space could be empty or filled, for example, with a gas or water-soluble material.

Figure 9:
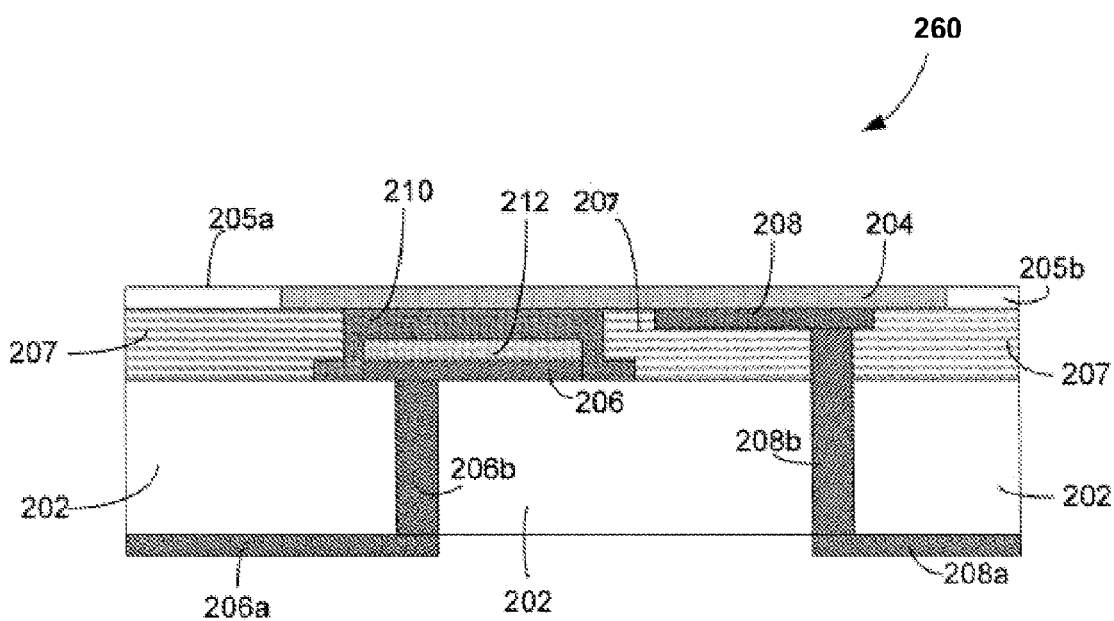
FIG. 9 is a cross-sectional view of still another embodiment of sensor device with the sensor electrodes disposed in a reservoir covered by a disintegratable reservoir cap, where the working electrode and counter electrode extend through vias in the substrate for electrical connection.

Another variation of the device is shown in FIG. 9. Device 260 includes substrate 202, reservoir cap 204, and a sensor built into structural material layer 207. The sensor comprises working electrode 206, counter electrode 208, semi permeable sensor membrane 210, and sensor chemical component 212. The working electrode 206 and counter electrode 208 are electrically connected to other device electronics through vias 206b, 208b and electrical traces 206a, 208a. In operation, electric current is passed through the reservoir cap 204 through input and out leads 205a and 205b to electrothermally ablate the reservoir cap, disintegrating it and exposing the sensor therebeneath. In this embodiment, there is no gap or space or biodegradable/water soluble material between the sensor and the reservoir cap.

Sensor Device Fabrication Methods

In another aspect, methods of fabricating sensor devices are provided. The devices described herein can be made by various processes. In one embodiment, the materials/layers are built up by a series of steps using deposition and etching techniques known in the art. Other fabrication and microfabrication methods known in the art that can be used or adapted to make the devices include lithography and etching, injection molding and hot embossing, electroforming/electroplating, microdrilling (e.g., mechanical drilling, laser drilling, ultrasonic drilling), micromilling, electrical discharge machining (EDM), photopolymerization, surface micromachining, high-aspect ratio methods (e.g., LIGA), micro stereo lithography, silicon micromachining, rapid prototyping, DEEMO (Dry Etching, Electroplating, Molding), and build-up or lamination techniques, such as LTCC (low temperature co-fired ceramics). See, for example, U.S. Pat. Nos. 6,123,861 and 6,808,522.

Figure 3:
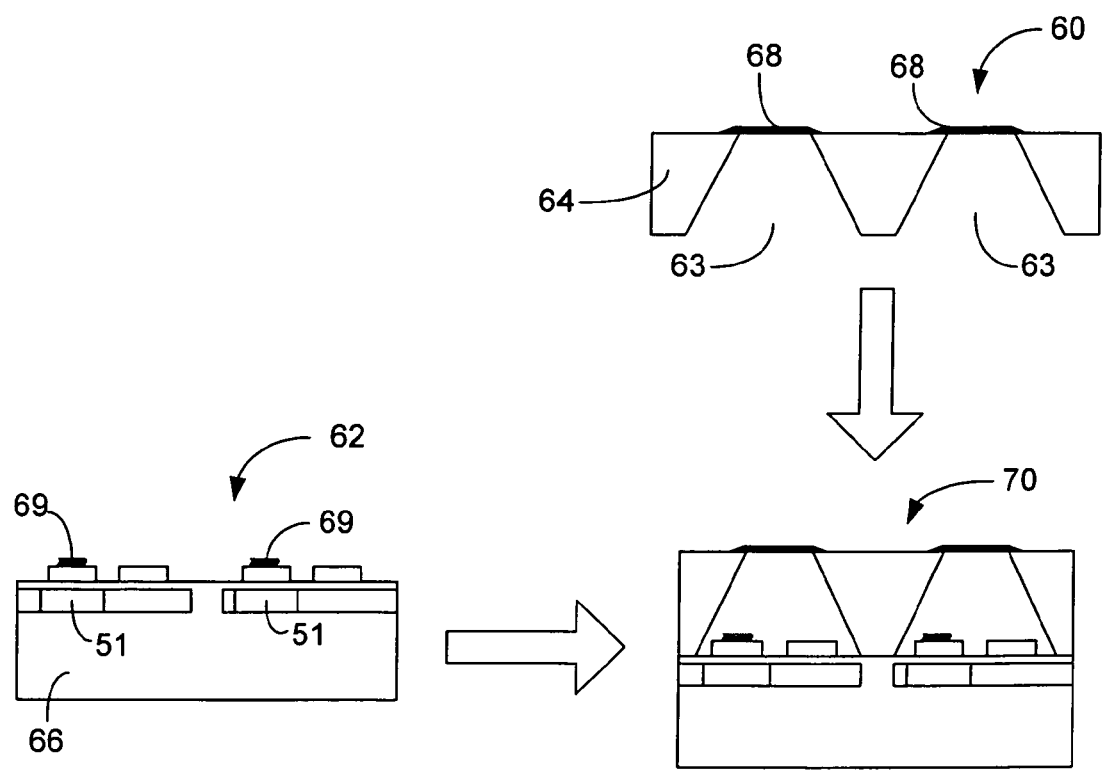
FIG. 3 is a cross-sectional view illustrating the steps of one embodiment of a method for assembling a multi-reservoir sensor device.

In one embodiment, illustrated in FIG. 3, a sensor substrate subpart 62 is fabricated, a reservoir/opening substrate subpart 60 is fabricated, and then the two subparts are bonded together to form a complete device 70 with sensors sealed inside reservoirs. The reservoir/opening substrate subpart 60 includes substrate portion 64, reservoirs 63, and reservoir caps 68 (with actuation circuitry not shown). The sensor substrate subpart 62 includes glucose sensors 69 (e.g., working and counter electrodes and glucose oxidase) and sensor deactivator fuses 51 on substrate portion 66. The bonding step requires avoidance of high temperatures that would prematurely damage the glucose oxidase. Bonding and hermetic sealing techniques which could be useful in fabricating the devices are described in U.S. patent application Publication No. 2003/0010808 to Uhland et al., and U.S. patent application Ser. No. 10/894,265, which are incorporated herein by reference. Other bonding techniques known in the art also could be used. In an alternative embodiment, the sensor and the protective component (i.e., the reservoir and opening mechanism) can be fabricated on a single substrate, requiring no bonding steps.

Multi-Unit Sensor and Drug Delivery Device

In another aspect, a medical device is provided that includes an implantable sensor portion (or sensor unit) and a separate drug delivery portion (or drug unit). The drug delivery portion can be implantable or designed to be worn externally. The sensor portion and the drug delivery portion operate together to sense in vivo a chemical entity or physiological condition and deliver one or more drugs as therapeutically indicated, based at least in part on a signal from the sensor portion. In a preferred embodiment, the sensor unit comprises a multi-reservoir device with reservoir-based sensors as described above and illustrated in FIGS. 1-5 and 7-9.

The device includes features for communication between the drug delivery portion and the sensor portion. In various embodiments, the communication is through tissue and/or air by transmission of digital/analog light, electromagnetic (e.g., RF), sonic/acoustic energy, hydraulic energy, or combinations thereof, with or without conductors. Examples of conductors include wire, optical fiber, and fluid-filled lumens for sonic or hydraulic energy conduction. In exemplary embodiments, the communication feature includes one or more of signal encoders/transducers, emitters, receivers, and decoders/transducers.

In embodiments where the two portions are tethered together, for example with a conductor such as a wire, the wire preferably is provided with mating hardware, such as a plug or other selectively disconnectable connector, which permits the two portions to be separated and connected as needed. Such a feature would be desirable, for example, when it is necessary to replace one portion (e.g., to replace a battery or to reload with drug) without disturbing the other portion, e.g., while leaving the implanted portion in the patient.

Figure 6:
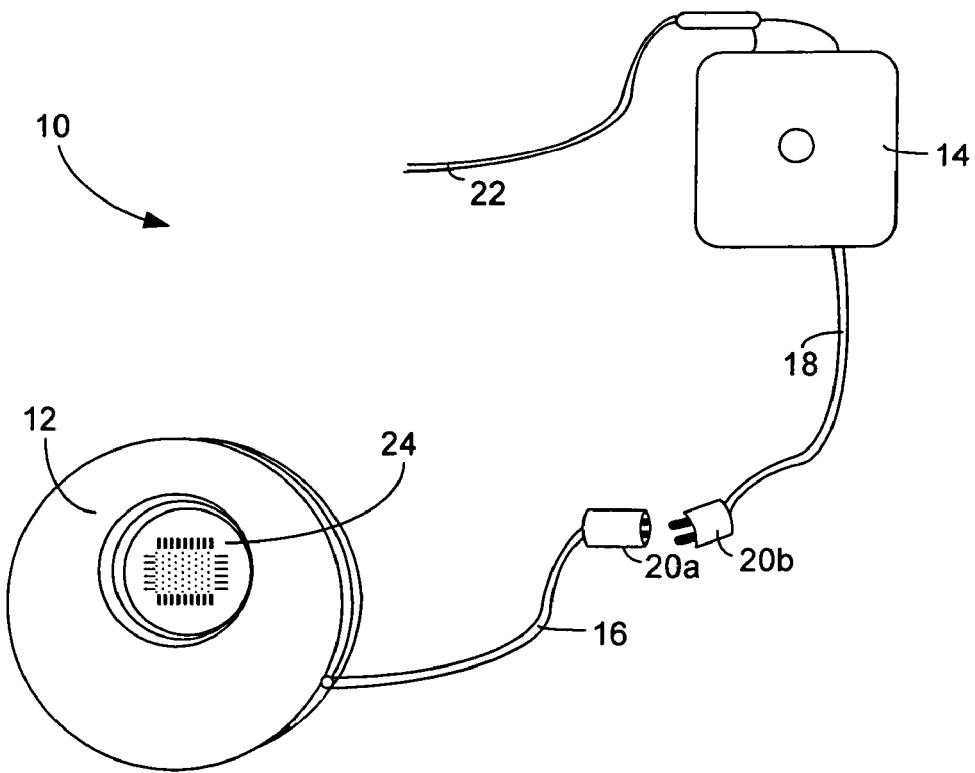
FIG. 6 is a perspective view of one embodiment of a medical device having an implantable sensor portion (or sensor unit) and a separate drug delivery portion (or drug unit).

An example of a two-portion device is illustrated in FIG. 6. It shows a device 10 which comprises a sensor unit 12 and a drug delivery unit 14, which are connected by wires 16 and 18, where wires 16 and 18 can be joined together by a female connector 20a and a male connector 20b. Drug delivery unit 14 is a pump which discharges drug through flexible catheter 22. Sensor unit 12 comprises an array of reservoirs 24, each of which contains a sensor. The sensor unit comprises a controller, which can relay instructions to the drug delivery unit 14 via wires 16 and 18.

In one embodiment, the drug unit comprises a fully implantable infusion pump (IIP), which is intended to provide long-term continuous or intermittent drug infusion. The route of administration can include intravenous, intra-arterial, subcutaneous, intraperitoneal, intrathecal, epidural, and intraventricular. Typically, the IIP is surgically placed in a subcutaneous pocket under the intraclavicular fossa or in the abdominal wall, and a catheter extending from the IIP is threaded into the therapeutically desirable location. In another embodiment, the drug unit is an externally worn infusion pump and provided with a catheter through the patient's skin. The pumps can operate by a number of driving mechanisms including peristalsis, fluorocarbon propellant, osmotic pressure, piezoelectric disk benders, or the combination of osmotic pressure with an oscillating piston. Representative examples drive mechanisms include those described in U.S. Pat. No. 6,805,693 to Gray et al., U.S. Pat. No. 6,554,800 to Nezhadian et al., and U.S. Pat. No. 6,375,638 to Nason et al.

In one embodiment, the drug delivery portion comprises a multi-reservoir device with an active release mechanism. In one example, the drug delivery portion comprises one or more microchip devices comprising an array of microreservoirs containing one or more drugs for release. In another example, the drug delivery portion comprises a microtube device or other device for accelerated release described in U.S. patent application Publication No. 2004/0106914 A1 to Coppeta, et al. In a further example, the drug delivery portion has a cylindrical or spherical body having one or more regions or surface areas over which multiple reservoirs, such as microreservoirs, are disposed.

In one embodiment, an apparatus is provided for use in the management of diabetes. The apparatus includes an insulin supply and delivery unit, a glucose-monitoring (sensing) unit, and a controller that communicates with both units. In one embodiment, the insulin supply and delivery unit (which can be externally worn or fully implantable) comprises (1) a refillable reservoir containing insulin, and (2) a pump for delivering the insulin to patient. In one embodiment, the glucose-monitoring unit comprises an array of discrete reservoirs each comprising individual glucose sensors covered by a selectively removable reservoir cap. The controller, which typically comprises a microprocessor, can be part of either the insulin delivery unit or the glucose-monitoring unit, or it can be a separate unit adapted to operably communicate with both the glucose sensors and the insulin delivery. The controller can monitor a patient's glucose level and can direct the insulin unit to deliver more or less insulin depending upon the monitored glucose level. The controller would make dosing decisions based on an acceptable algorithm. The controller also can monitor the accuracy and stability of each glucose sensor. When it senses that the active sensor is not reading properly (e.g., because it has become fouled), then the controller can direct the monitoring unit to open another reservoir to expose a new sensor. The controller optionally can direct the destruction of the old sensor to avoid potential interference with operation of the new one.

In another embodiment, a medical device is provided for use in the treatment of cancer or hormone therapy, where long-term drug delivery is needed and an in vivo sensor can be used to monitor physiological chemical or condition useful in determining the appropriate dosage of therapeutic agent to deliver.

ADDITIONAL DESCRIPTION OF THE DEVICES

In preferred embodiments, the sensing device includes a substrate having a plurality of reservoirs, which contain sensors, and optionally drug molecules for release. The substrate, reservoirs, reservoir caps, control circuitry, and power source are described herein and in U.S. Pat. Nos. 5,797,898, 6,123,861, 6,551,838, 6,491,666, and 6,527,762, as well as U.S. Patent Application Publications No. 2002/0138067, No. 2002/0072784, No. 2002/0151776, and No. 2002/0107470. In one embodiment, control of reservoir cap opening includes electro-thermal ablation techniques, as described in U.S. Patent Application Publication No. 2004/0121486 to Uhland, et al., which is incorporated herein by reference. The device may be a microchip device, or the reservoirs/sensors/reservoir caps can be integrated into another type of device.

At times herein, the term "reservoir device" is used to refer to the device comprising a substrate and reservoirs, as distinguished from the "secondary device," which is disposed in the reservoirs of the reservoir device.

Substrate and Reservoirs

The substrate is the structural body (e.g., part of a device) in which, or on which, the reservoirs are formed. A reservoir can be a well, a container, or other space in which reservoir contents are stored, as described above. MEMS methods, micromolding, and micromachining techniques known in the art can be used to fabricate the substrate/reservoirs from a variety of materials. See, for example, U.S. Pat. No. 6,123,861 and U.S. Patent Application Publication No. 2002/0107470.

Examples of suitable substrate materials include metals, ceramics, semiconductors, and degradable and non-degradable polymers. Biocompatibility of the substrate material typically is preferred for in vivo device applications. The substrate, or portions thereof, may be coated, encapsulated, or otherwise contained in a biocompatible material (e.g., poly (ethylene glycol), polytetrafluoroethylene-like materials, inert ceramics, diamond-like materials, titanium, and the like) before use. In one example, the substrate is formed of silicon. In one embodiment, the substrate is hermetic, that is impermeable (at least during the time of use of the reservoir device) to the molecules to be delivered and to surrounding gases or fluids (e.g., water, blood, electrolytes or other solutions). In another embodiment, the substrate is made of a strong material that degrades or dissolves over a defined period of time into biocompatible components. Examples of biocompatible polymers include poly(lactic acid)s, poly(glycolic acid)s, and poly(lactic-co-glycolic acid)s, as well as degradable poly(anhydride-co-imides). The substrate may consist of only one material, or may be a composite or multi-laminate material, that is, composed of several layers of the same or different substrate materials that are bonded together.

The substrate can be flexible or rigid, and it can be in various shapes and have a range of differently shaped surfaces. The substrate may, for example, be in a shape selected from disks, cylinders, or spheres. For example, it can have a first side for release/exposure of reservoir contents and a second, opposite side, wherein the release side is shaped to conform to a curved tissue surface or into a body lumen and the back side (distal the release side) is shaped to conform to an attachment surface.

The substrate thickness can vary depending upon the particular device and application using the activation system described herein. For example, the thickness of a device may vary from approximately 10 µm to several millimeters (e.g., 500 µm). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, although other constraints such as manufacturing limitations or total device size limitations (e.g., for implantation into a patient) also may be important design factors. For example, devices for in vivo applications desirably would be small enough to be implanted using minimally invasive procedures, such as via a trochar or injection technique.

The substrate includes at least two and preferably tens or hundreds of reservoirs. The substrate could include, for example, 200 to 400 reservoirs, each containing a sensor. For simplicity, only one or two reservoirs are shown in the Figures herein; however, it is understood that a device, particularly an implantable medical device preferably would contain an array of many more reservoirs.

In one preferred embodiment, the reservoir has a volume equal to or less than 500 µL (e.g., less than 250 µL, less than 100 µL, less than 50 µL, less than 25 µL, less than 100 µL, etc.) and greater than about 1 nL (e.g., greater than 5 nL, greater than 10 nL, greater than about 25 nL, greater than about 50 nL, greater than about 1 µL, etc.). In still other embodiments, particularly where the area for sensor exposure desirably is large, the volume of the reservoir is larger than 500 µL. In such embodiments, a single reservoir may preferably include two or more reservoir caps, as described in U.S. Patent Application No. 60/606,387, which is incorporated herein by reference.

Sensor and Other Reservoir Contents

The devices contain sensors, sensor components, or other devices or device components that need to be protected from surrounding environmental components until their exposure is desired. These sensors, sensor components, or other devices or device components are sometimes referred to herein as "secondary devices." The reservoirs may alternatively or additionally include other reservoir contents such as reacting components.

In a preferred embodiment, the secondary device is a sensor or sensing component. As used herein, a "sensing component" includes a component utilized in measuring or analyzing the presence, absence, or change in a chemical or ionic species, energy, or one or more physical properties (e.g., pH, pressure) at a site. Types of sensors include biosensors, chemical sensors, physical sensors, or optical sensors. Preferred sensors measure properties such as biological activity, chemical activity, pH, temperature, pressure, optical properties, radioactivity, and electrical conductivity. Other possible properties to measure include glucose and blood gases, such as oxygen and carbon dioxide. These may be discrete sensors (e.g., "off-the-shelf" sensors) or sensors integrated into or onto the substrate. Biosensors typically include a recognition element such as an enzyme or antibody or nucleic acid. The transducer used to convert the interaction between the analyte and recognition element into an electronic signal may be, for example, electrochemical, optical, piezoelectric, or thermal in nature. Representative examples of biosensors constructed using microfabrication methods are described in U.S. Pat. Nos. 5,200,051; 5,466,575; 5,837,446; and 5,466,575 to Cozzette, et al.

In one embodiment, the sensor comprises a differential oxygen sensor or other sensor known in the art that has two (or more) working electrodes. For example, glucose oxidase or other enzyme can be immobilized on one working electrode and not on a second working electrode and the differential between the detection levels is used to determine concentration of an analyte. See, for example, U.S. Pat. No. 6,498,043, which is expressly incorporated herein by reference.

The devices also can store and expose any combination of chemicals and devices. For example, each reservoir can contain a different chemical or molecule for release. In one embodiment, the chemical contained in the reservoir is an enzyme, glucose oxidase, which is used in some glucose sensing devices. In another embodiment, the device reservoirs contain another type glucose sensor.

It is also understood that multiple devices having completely different functions can be placed inside or near each reservoir of the device. For example, three sensors for detecting and quantifying three molecules can be located in the same reservoir, while three completely different sensors for detecting three different molecules can be placed in a neighboring reservoir. Alternatively, a single device may be comprised of three components, each of which is located in a different reservoir. With this technology, a medical device has the ability to selectively expose each chemical, device, or device component to the environment outside of the reservoir and to vary the number and type of chemicals and devices associated with each reservoir.

There are several different options for receiving and analyzing data obtained with devices located in the reservoir devices. First, the output signal from the device can be recorded and stored in writeable computer memory chips. Second, the output signal from the device can be directed to a microprocessor for analysis and processing. Third, the signal can be sent to a remote location away from the reservoir device. For example, the reservoir device can be provided with a transmitter (RF, ultrasound, magnetic, etc.) in order to transmit a signal (e.g., data) from the reservoir device to a computer or other remote receiver. The reservoir device can also be controlled using the same or similar transmission mechanisms. Power can be supplied to the reservoir device locally by a battery or remotely by wireless transmission.

As used herein, unless explicitly indicated otherwise, the term "reacting component" includes any chemical species which can be involved in a reaction, including reagents; catalysts, including enzymes, metals, and zeolites; proteins; nucleic acids; polysaccharides; polymers; cells; as well as organic or inorganic molecules, including diagnostic agents. The reacting component contained within a reservoir may be present in any form (e.g., solid, liquid, gel, or vapor). It may be present in the reservoir in pure form or as a mixture with other materials. For example, the chemicals may be in the form of solid mixtures, such as amorphous and crystalline mixed powders, porous or nonporous monolithic solid mixtures, and solid interpenetrating networks; liquid mixtures or solutions, including emulsions, colloidal suspensions, and slurries; and gel mixtures, such as hydrogels. When the reservoir cap is removed from a reservoir, the chemicals inside the reservoir can remain in the reservoir or can be released from the reservoir.

In one embodiment wherein the chemicals remain in the reservoir, the chemicals are zeolites used for a heterogeneous reaction. When the reservoir cap is removed, the reagents diffuse into the reservoir to react at the surface or in the interior of the zeolite catalyst, which remains in the reservoir.

The material in the reservoir can include one or more lyophilized components. Such lyophilized materials can be loaded into the reservoir following lyophilization or alternatively a fluid component containing the material can be loaded into the reservoirs and then subsequently lyophilized.

In one embodiment, the device includes one or more biosensors (which may be sealed in reservoirs until needed for use) that are capable of detecting and/or measuring signals within the body of a patient. As used herein, the term "biosensor" includes sensing devices that transduce the chemical potential of an analyte of interest into an electrical signal (e.g., an ion selective field effect transistor or ISFET), as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or mechanical loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

In a preferred embodiment, the reservoir contents further include a confining layer incorporated between the sensor or a reagent and the space above. The confining layer permits transport of an analyte to reach the reagent or sensor, prevents one or more non-analyte substances from contacting the reagent or sensor, and secures or contains the sensor/reagent to prevent dissipation into the body, which may degrade the sensor/reagent or may be deleterious to the patient's body. In some embodiments, the confining layer is a polymer, a microporous structure, or a hydrogel.

Reservoir Caps

As used herein, the term "reservoir cap" includes a membrane or other structure suitable for separating the contents of a reservoir from the environment outside of the reservoir. It generally is self-supporting across the reservoir opening. The devices, however, can further include additional structures fabricated to provide mechanical support to the reservoir cap. In another embodiment, the reservoir cap is supported by or resting directly or indirectly on the material to be covered/protected, such as the drug formulation or biosensor.

In another embodiment, multiple reservoir caps may be located over an individual reservoir and supported by a grid structure, as described in U.S. Patent Application No. 60/606,387, which is incorporated herein by reference. Such multiple caps allow a larger area of the reservoir to be exposed than may be feasible using a single large cap. For example, opening a large cap may require more power or generation of more heat that could damage tissue or sensors compared to opening several smaller caps. Smaller caps may be opened simultaneously or sequentially.

Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" is used broadly to include without limitation degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegrate" or "rupture" of the reservoir cap is conducted by a mechanism described in U.S. Pat. Nos. 6,527,762 or 6,491,666. In yet another specific embodiment, the "disintegration" is by an electro-thermal ablation technique, as described in U.S. patent application Publication No. 2004/0121486 to Uhland, et al. These patents and applications are expressly incorporated herein by reference.

In active release devices, the reservoir cap generally includes any material that can be disintegrated or permeabilized in response to an applied stimulus, e.g., electric field or current, magnetic field, change in pH, or by thermal, chemical, electrochemical, or mechanical means.

In one embodiment, the reservoir cap is a thin metal film and is impermeable to the surrounding environment (e.g., body fluids or another chloride containing solution). In one variation, a particular electric potential is applied to the metal reservoir cap, which is then oxidized and disintegrated by an electrochemical reaction, to expose the sensor located in the reservoir. Examples of suitable reservoir cap materials include gold, silver, copper, and zinc.

In another variation, the reservoir cap is heated (e.g., using resistive heating) to cause the reservoir cap to melt and be displaced from the reservoir to open it. This latter variation could be used, for example, with reservoir caps formed of a metal or a non-metal material, e.g., a polymer. In yet another variation, the reservoir cap is formed of a polymer or other material that undergoes a temperature-dependent change in permeability such that upon heating to a pre-selected temperature, the reservoir cap is rendered permeable to molecules involved in the sensing function.

In still another embodiment, the reservoir cap is formed of a conductive material, such as a metal film, through which an electrical current can be passed to electrothermally ablate it, as described in U.S. patent application Publication No. 2004/0121486 to Uhland, et al. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a multi-layer structure, such as a multi-layer/laminate structure of platinum/titanium/platinum. The reservoir cap is operably (i.e., electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (ruptured or disintegrated).

In passive opening devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes.

Any combination of passive and/or active reservoir-opening mechanisms can be used.

Controlling Sensor Exposure

The device preferably is provided with a control means to control the time at which the reservoir is opened and/or the sensor exposed. The particular features of the control means depend on the mechanism of reservoir cap activation described herein.

For example, the control means can include the hardware, electrical components, and software needed to control and deliver the electric current from a power source to selected reservoir caps for actuation (i.e., opening). The control means can include an input source, a microprocessor, a timer, a demultiplexer (or multiplexer), and a power source. As used herein, the term "demultiplexer" also refers to multiplexers. The power source provides energy to activate the selected reservoir. For example, the operation of the reservoir opening system can be controlled by an on-board microprocessor (e.g., the microprocessor is within an implantable or insertable device). The microprocessor can be programmed to initiate the disintegration or permeabilization of the reservoir cap at a pre-selected time or in response to one or more of signals or measured parameters, including receipt of a signal from another device (for example by remote control or wireless methods) or detection of a particular condition using a sensor such as a biosensor. In another embodiment, a simple state machine is used, as it typically is simpler, smaller, and/or uses less power than a microprocessor. The device can also be activated or powered using wireless means, for example, as described in U.S. 20020072784 A1 to Sheppard et al. In one embodiment, the activation means comprises one or more capacitors. For instance, capacitors could be used in the thermal ablation reservoir opening circuitry. In another embodiment, the activation means comprises power and data transmission means that include the use of modulated ultrasonic energy. See, e.g., U.S. Pat. No. 6,432,050 to Porat et al.

In one embodiment, the device includes a substrate having a two-dimensional array of reservoirs arranged therein, anode reservoir caps covering each of the reservoirs, cathodes positioned on the substrate near the anodes, and means for actively controlling disintegration of the reservoir caps. The means includes a power source and circuitry to control and deliver an electrical potential energy. That is, the control circuitry can have potentiostat/galvanostat functionality to drive a reaction between selected anodes and cathodes. Upon application of a potential between the electrodes, electrons pass from the anode to the cathode through the external circuit causing the anode material (reservoir cap) to oxidize and dissolve into the surrounding fluids, exposing the sensor to the surrounding fluids, e.g., in vivo. The microprocessor directs power to specific electrode pairs through a demultiplexer as directed by an EPROM, remote control, or biosensor.

In another embodiment, the control means controls electro-thermal ablation of the reservoir cap. For example, the device could include a reservoir cap formed of an electrically conductive material; an electrical input lead connected to the reservoir cap; an electrical output lead connected to the reservoir cap; and a control means to deliver an effective amount of electrical current through the reservoir cap, via the input lead and output lead, to locally heat and rupture the reservoir cap to expose the sensor. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed.

In one embodiment using the electrothermal ablation opening mechanism, the reservoirs are arrayed in the substrate in a square matrix (e.g., four or more reservoirs positioned in a two-dimensional array), with the input side of the reservoir caps electrically connected in parallel by row, and the output side of the reservoir caps electrically connected in parallel by column. The conductor material also can form input leads, output leads, and reservoir caps. In an alternative design, which still uses the interconnected rows and columns, the reservoir caps are formed of a different material than the leads (or rows or columns of conductor material). An insulating material is provided at the intersection of the columns and rows to prevent short-circuiting. The insulating material can be provided between the upper surface of the column and the lower surface of the row. This embodiment provides a matrix-addressed array with significantly reduced input/output (I/O) requirements. The electrically conductive reservoir caps form electrical connections between the rows and columns of the array. When applying a voltage/current to a designated row and column to activate the reservoir cap at the intersection of the row and column, the connections cause current to flow through other reservoir caps. In one embodiment, additional rows and columns can be added to the array, and conducting elements added at each of the intersections, to prevent an operable reservoir cap from being exposed to relatively large unintended currents, which might cause premature rupture. These additional conductors could be made of the same material as the reservoir caps, but would not be located over reservoirs. In another approach, the reservoir caps are designed to rupture without creating an open circuit (to retain essentially the same electrical resistance) between the input and output leads. In embodiments where the passage of current through non-addressed reservoir caps in the array is undesirable, a rectifying element, such as a diode, can be added in series connection with each reservoir cap, to eliminate unintended currents. The diode could be a semiconductor junction diode or a Schottky barrier diode. If a silicon substrate is used in the controlled release device, then the substrate and rectifying element could be integrally formed. The processes of introducing impurities into semiconductors to modify its conductivity and majority charge carrier, such as diffusion or ion implantation, and creating metal to semiconductor contacts, are well known. These could be integrated into the reservoir device fabrication process. Alternatively, specific activation of a reservoir cap can be accomplished by integrating a transistor with each reservoir cap. In one embodiment, such a matrix approach is accomplished with transistors. Where transistors are integrated onto a microchip substrate, other active electronic components such as multiplexing switches optionally may also be able to be integrated into the reservoir device.

Microelectronic device packages are typically made of an insulating or dielectric material such as aluminum oxide or silicon nitride. Low cost packages can also be made of plastics or reinforced epoxies (similar to those used in making printed circuit boards). Their purpose is to allow all components of the device to be placed in close proximity and to facilitate the interconnection of components to power sources and to each other, while protecting the electronics from the environment. Implantable reservoir device packages typically are hermetically sealed, e.g., in a titanium encasement, which essentially exposes only the reservoir caps.

The control means can include a microprocessor, a timer, a demultiplexer, and an input source (for example, a memory source, a signal receiver, or a biosensor), and a power source. The timer and demultiplexer circuitry can be designed and incorporated directly onto the surface of the microchip during electrode fabrication, or may be incorporated in a separate microchip. The criteria for selection of a microprocessor are small size, low power requirement, and the ability to translate the output from memory sources, signal receivers, or biosensors into an address for the direction of power through the demultiplexer to a specific reservoir on the microchip device. Selection of a source of input to the microprocessor such as memory sources, signal receivers, or biosensors depends on the microchip device's particular application and whether device operation is preprogrammed, controlled by remote means, or controlled by feedback from its environment (i.e., biofeedback).

A microprocessor is used in conjunction with a source of memory such as erasable programmable read only memory (EPROM), a timer, a demultiplexer, and a power source such as a battery or a biofuel cell. A programmed sequence of events including the time a reservoir is to be opened and the location or address of the reservoir is stored into the EPROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

USES OF THE DEVICES

The devices have numerous in vitro and in vivo applications. The devices can be used in a variety of applications in which it is desired to selectively expose sensors or other secondary devices, or release discrete quantities of drug or other chemical molecules. Applications include controlled or selective, on-demand sensing, for example to detect the presence or absence of a type of molecule, to test for biological activity or reactivity of molecules exposed to the sensor, or to measure parameters, such as pH, temperature, reactivity with another molecule, optical properties (e.g., refractive index, color, or fluorescence), radioactivity, pressure, or electrical conductivity. In one embodiment, the sensor employs an optical fiber that can be used to sense changes in optical properties in or near the reservoirs, changes which might occur, for example, due to a reaction in the reservoir or in the environment adjacent the reservoir. In a related embodiment, the reservoir contains a scintillation fluid to aid in the (optical) detection of radioactive materials.

The present devices are particularly useful in applications where prolonged exposure of a catalyst to the environment results in decreased performance of the catalyst due to "fouling" or coating of the catalyst surface or due to chemical degradation of the catalyst. The devices would enable many discrete quantities of catalyst to be contained in one small device, with each quantity available independently when needed. For example, if the catalyst of a first reservoir becomes fouled, then a second reservoir can be opened to expose fresh catalyst, and repeated for any number of reservoirs. Furthermore, different catalysts can be provided in different reservoirs of a single device, thereby enhancing the range of reactions that can be catalyzed with a single device.

In a preferred embodiment, the device contains sensors for use in glucose monitoring and insulin control. Information from the sensor could be used to actively control insulin release from the same device or from a separate insulin delivery device (e.g., a conventional insulin pump, either implanted or externally-worn).

In one embodiment, an implantable medical device has reservoirs in which pairs of sensors are stored for selective exposure: a reference sensor and a working sensor. The reference sensor is used to check the operation of the working sensor. A microprocessor, powered by a power source, can be programmed to continuously compare, e.g., using voltmeters or other instrumentation, the operation of the working sensor to the reference sensor in a reservoir. If a first sensor in a first reservoir is not operating properly, a signal can be sent back to the microprocessor, which, in turn, can activate a second reservoir to expose a new pair of electrodes. Optionally, the microprocessor can send a signal to a transmitter to notify a remotely located computer that one less operational sensor remains or to signal other operational information.

In another embodiment, a present state of the patient is measured by the device and compared to a reference state by statistical and medically relevant criteria. Subsequent programs of sensing and/or drug delivery by the sensing device and/or by a separate drug delivery device are dependent upon the outcome of the comparison.

The present devices also can be used in vitro to selectively expose secondary devices or device components, reacting components, or both to the surrounding environment or components thereof, particularly in the fields of analytical chemistry and medical diagnostics. For some in vitro applications, the devices can release small, controlled amounts of chemical reagents or other molecules into solutions or reaction mixtures at precisely controlled times and rates. In others, secondary devices such as sensors can be protected from the surrounding environment until they are needed. For example, the catalyst (i.e., enzyme) can be protected in the reservoir from the surrounding environment until it is desired to expose the enzyme and catalyze the reaction of interest.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:
1. A device for the controlled exposure of a secondary device, comprising:
 a substrate having a reservoir;
 an operational secondary device in the reservoir;
 one or more reservoir caps covering the reservoir to isolate the secondary device from an environmental component outside the reservoir, wherein the one or more reservoir caps are impermeable to the environmental component;

means for disintegrating or permeabilizing the one or more reservoir caps to expose the secondary device to the environmental component; and a resistive heater for selectively rendering the secondary device inoperable.

2. The device of claim 1, wherein the means for disintegrating or permeabilizing comprises a microprocessor programmed to initiate said disintegrating or permeabilizing at a specified time, upon receipt of a signal from another device, or upon detection of a specified sensed condition.

3. The device of claim 1, wherein the secondary device comprises a sensor or a sensing component.

4. The device of claim 3, wherein the sensor or sensing component comprises a glucose sensor.

5. The device of claim 4, wherein the sensor or sensing component comprises glucose oxidase.

6. The device of claim 3, wherein the sensor or sensor component comprises an enzyme and the resistive heater generates heat effective to deactivate the enzyme.

7. A method for detecting or measuring a property at a site, the method comprising the steps of:
providing at the site the device of claim 3; and
disintegrating or permeabilizing the one or more reservoir caps, using the means for disintegrating or permeabilizing, to expose the sensor or sensing component in the reservoir; and
detecting or measuring a property in or adjacent to the exposed sensor or sensing component.

8. The method of claim 7, further comprising the step of rendering the sensor or sensing component inoperable by passing an electric current through the resistive heater.

9. The method of claim 7, wherein the sensor or sensing component is a glucose sensor.

10. The device of claim 6, wherein the enzyme comprises a glucose oxidase.

11. The device of claim 3, wherein the sensor or sensing component comprises at least one working electrode, a counter electrode, an enzyme provided on the at least one working electrode, and a semipermeable membrane covering the enzyme and at least part of the at least one working electrode.

12. The device of claim 1, wherein the substrate is monolithic.

13. The device of claim 1, further comprising a biodegradable intermediary material disposed in the reservoir underneath the one or more reservoir caps and covering the secondary device.

14. The device of claim 1, further comprising a thin layer of a structural material underneath the one or more reservoir caps and an evacuated or gas-filled space in the reservoir between the secondary device and the structural material layer.

15. The device of claim 1, wherein the substrate comprises two or more portions bonded together.

16. A medical device comprising:
an implantable sensor unit which comprises the device of claim 1, wherein the secondary device comprises a sensor; and
a drug delivery unit comprising at least one therapeutic agent for release,
wherein the drug delivery unit is in communication with the implantable sensor unit and releases the therapeutic agent in response to the sensor's sensing of the environmental component.

17. A device for the controlled exposure of a secondary device, comprising:
a substrate having a reservoir;
a secondary device in the reservoir;
one or more reservoir caps covering the reservoir to isolate the secondary device from an environmental component outside the reservoirs, wherein the one or more reservoir caps are impermeable to the environmental component;
a biodegradable intermediary material disposed in the reservoir underneath the one or more reservoir caps and covering the secondary device; and
means for disintegrating or permeabilizing the one or more reservoir caps to expose the biodegradable intermediary material to a fluid from outside the device to cause the biodegradable intermediary material to disintegrate to expose the secondary device to the environmental component.

18. The device of claim 17, further comprising a layer of a structural material underneath the one or more reservoir caps and disposed between the biodegradable intermediary material and the one or more reservoir caps.

19. The device of claim 18, wherein the structural material comprises a dielectric material.

20. The device of claim 17, wherein the biodegradable intermediary material comprises a water-soluble solid, liquid, or gel.

21. The device of claim 17, wherein the biodegradable intermediary material comprises a polyethylene glycol, a polyethylene oxide, or a copolymer of poly (lactic-co-glycolic) acid.

22. The device of claim 17, wherein the secondary device comprises a sensor or sensing component.

23. The device of claim 22, wherein the sensor or sensing component comprises a glucose sensor.

24. The device of claim 22, wherein the sensor or sensing component comprises glucose oxidase.

25. The device of claim 22, wherein the sensor or sensing component comprises at least one working electrode, a counter electrode, an enzyme provided on the at least one working electrode, and a semipermeable membrane covering the enzyme and at least part of the at least one working electrode.

26. The device of claim 17, further comprising a means for selectively rendering the secondary device inoperable.

27. A medical device comprising:
an implantable sensor unit which comprises the device of claim 17, wherein the secondary device comprises a sensor; and
a drug delivery unit comprising at least one therapeutic agent for release,
wherein the drug delivery unit is in communication with the implantable sensor unit and releases the therapeutic agent in response to the sensor's sensing of the environmental component.

28. The device of claim 17, wherein the reservoir is a microreservoir.

* * * * *